(12) United States Patent
Gupta

(10) Patent No.: US 7,547,454 B2
(45) Date of Patent: Jun. 16, 2009

(54) HYDROXY ACID COMPLEXES FOR ANTIAGING AND SKIN RENOVATION

(76) Inventor: Shyam K Gupta, 5221 E. Windrose Dr., Scottsdale, AZ (US) 85254

( * ) Notice: Subject to any disclaimer, the term of this patent is extended or adjusted under 35 U.S.C. 154(b) by 536 days.

(21) Appl. No.: 11/309,441

(22) Filed: Aug. 6, 2006

(65) Prior Publication Data

US 2007/0092461 A1    Apr. 26, 2007

Related U.S. Application Data

(63) Continuation-in-part of application No. 11/307,729, filed on Feb. 18, 2006, and a continuation-in-part of application No. 10/439,349, filed on May 15, 2003, now abandoned, and a continuation-in-part of application No. 10/290,933, filed on Nov. 7, 2002, now abandoned.

(51) Int. Cl.
*A61N 33/32*    (2006.01)

(52) U.S. Cl. ..................................... 424/642

(58) Field of Classification Search ...................... None
See application file for complete search history.

(56) References Cited

OTHER PUBLICATIONS

Martin et al. in Bulliten de Societie Chemique de France 1963.*

* cited by examiner

*Primary Examiner*—Eric E. Silverman

(57) ABSTRACT

This invention relates to certain divalent and polyvalent d-orbital metals of first transition series of the Periodic Table of Elements, from Group IV to Group VI, and including Molybdenum, complexed concurrently with an amino acid, or an equivalent of an amino acid, and a hydroxy acid in a novel spirocyclic bidentate chemical complex form (FIG. 1). Upon topical application said metal complexes undergo enhanced skin penetration without causing skin irritation. The said metal complexes are useful for topical conditions that include dry skin, xerosis, ichthyosis, dandruff, brownish spots, keratoses, melasma, lentigines, age spots, dark circles around eyes, skin pigmentation, topical inflammation, liver spots, pigmented spots, wrinkles, blemishes, skin lines, oily skin, acne, warts, eczema, pruritic skin, psoriasis, inflammatory dermatoses, disturbed keratinization, dandruff, bacterial infection, fungal infection, wound healing, body odor, and skin changes associated with aging.

21 Claims, 7 Drawing Sheets

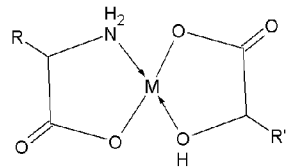
Metal [Amino Acid Alpha-Hydroxy Acid] Complex
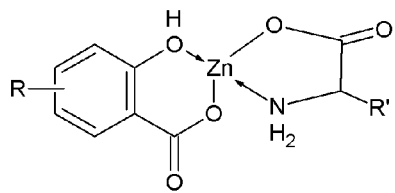
Metal [Amino Acid Beta-Hydroxy Acid] Complex
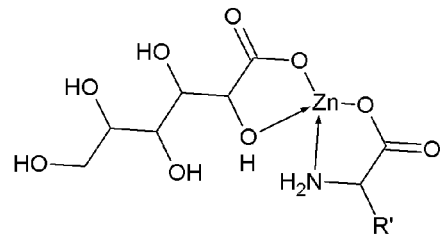
Metal [Amino Acid - Polyhydroxy Acid] Complex
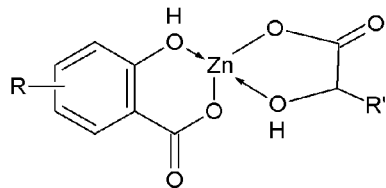
Metal [Alpha-Hydroxy Acid - Beta Hydroxy Acid Complex]
M = Divalent or Polyvalent Metal (Ti, V, Cr, Mn, Fe, Co, Ni, Cu, Zn, Ga, Ge, As, Se, Mo)
R , R'= Various Substituents
Figure 1. Metal Hydroxy Acid Complexes

Structure I

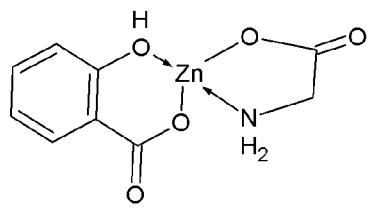

Chemical Name: [(Amino-k*N*)acetato-κ*O*][2-(hydroxy-k*O*)benzoato-κ*O*] Zinc

Adopted Name: Zinc Glycinate Salicylate Complex

Structure II

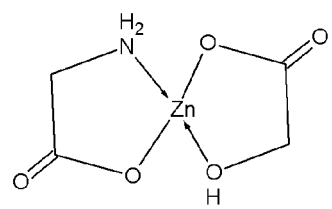

Chemical Name: [(Amino-κ*N*)acetato-κ*O*][(hydroxy-κ*O*)acetato-κ*O*] Zinc

Adopted Name: Zinc Glycinate Glycolate Complex

Structure III

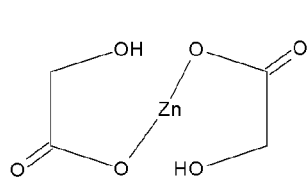

Chemical Name: Zinc Bis-(2-Hydroxyacetate)

Common Name: Zinc Glycolate

Structure IV

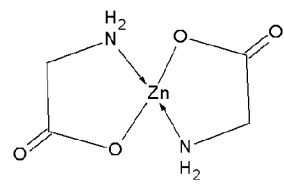

Chemical Name: Zinc Bis-Glycinate

Common Name: Zinc Glycinate

Figure 2. Nomenclature of Chemical Structures

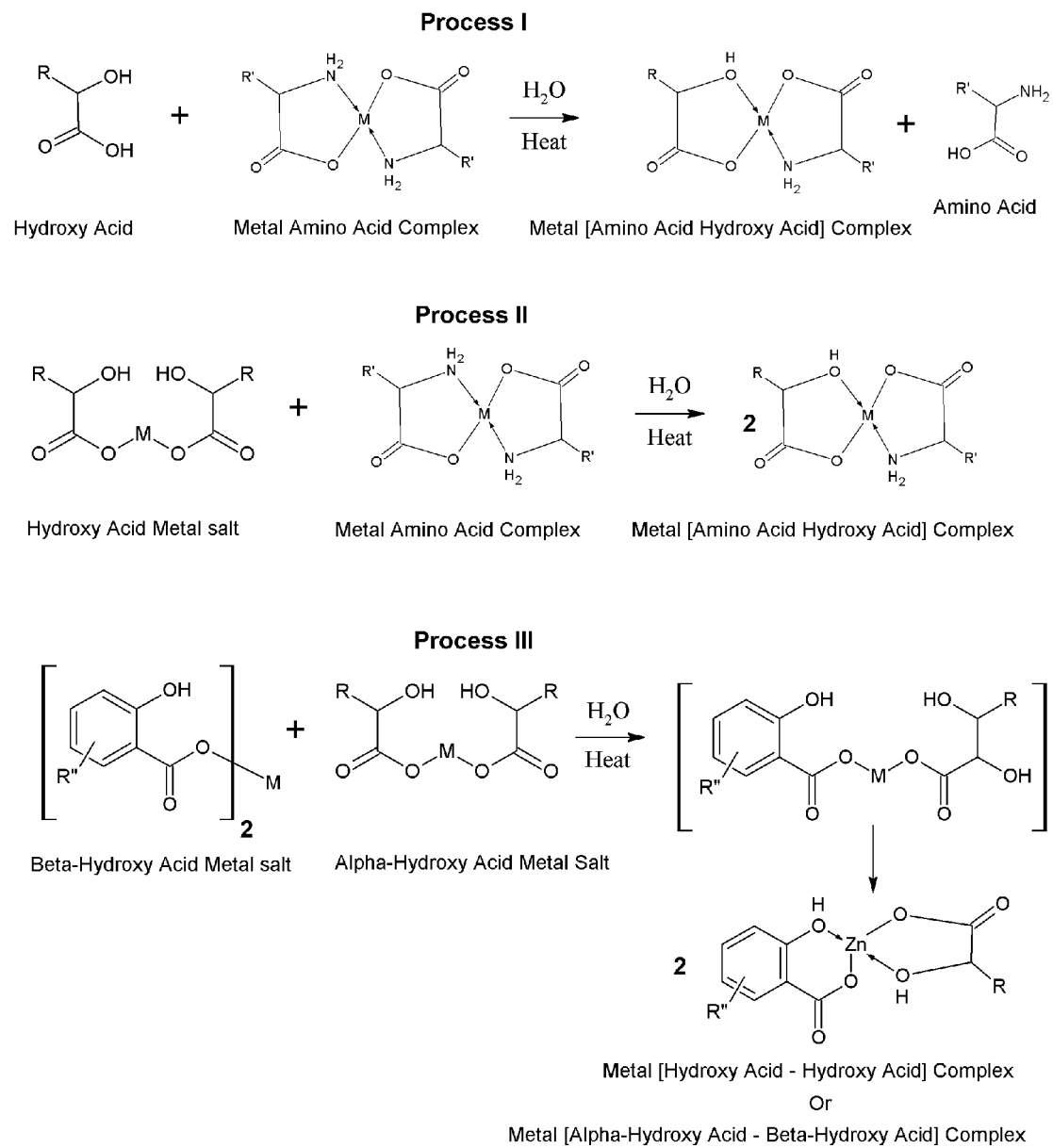
Figure 3. Processes for Metal [Amino Acid Hydroxy Acid] Complex and Metal [Hydroxy Acid - Hydroxy Acid] Complex

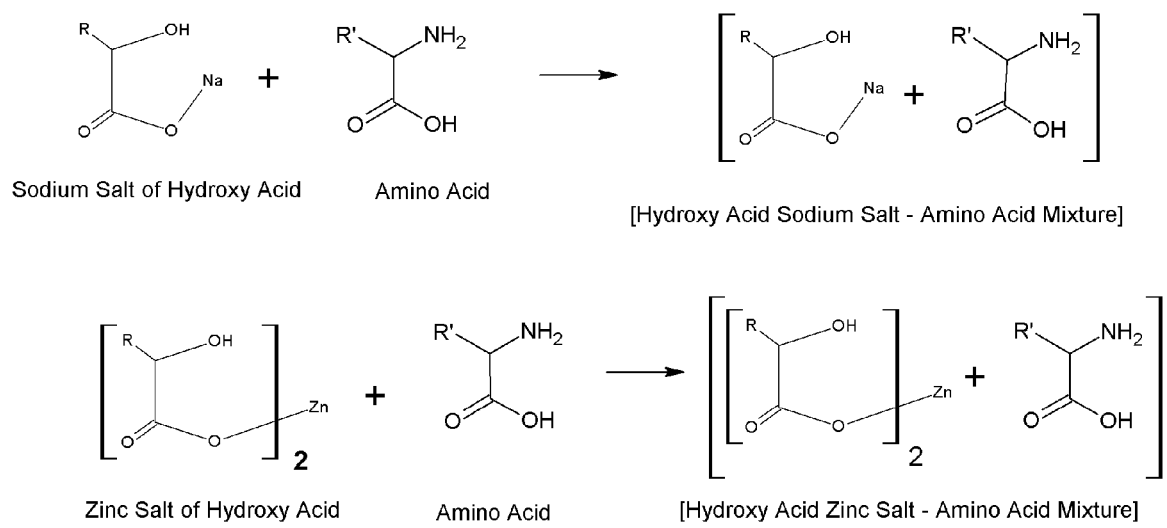
Figure 4. Yu Composition for Hydroxy Acid Salt and Amino Acid Combination

Ionization Scheme A
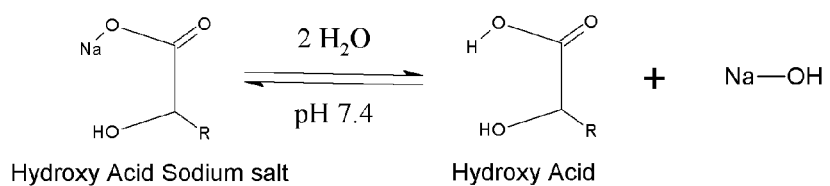
Hydroxy Acid Sodium salt       Hydroxy Acid
Ionization Scheme B
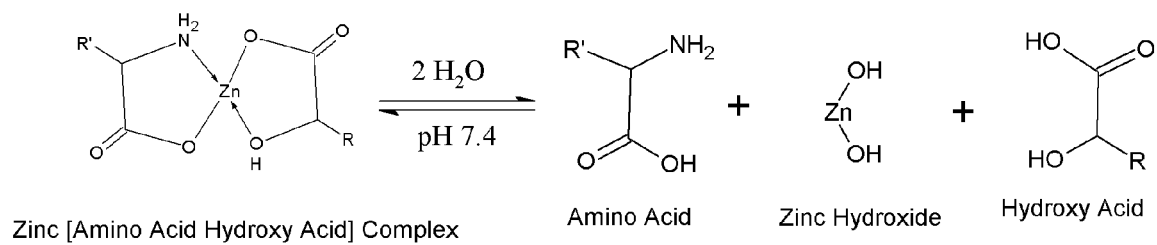
Zinc [Amino Acid Hydroxy Acid] Complex     Amino Acid     Zinc Hydroxide     Hydroxy Acid
Figure 5. Ionization of Hydroxy Acid Sodium Salt
and Zinc [Amino Acid Hydroxy Acid] Complex

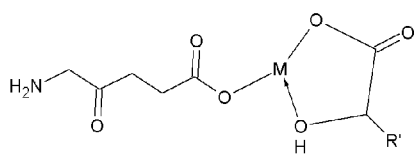
Metal [5-Amino Levulanic Acid - Alpha Hydroxy Acid] Complex
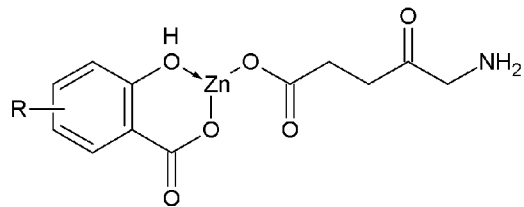
Metal [5-Amino Levulinic Acid - Beta Hydroxy Acid] Complex
M = Divalent or Polyvalent Metal (Ti, V, Cr, Mn, Fe, Co, Ni, Cu, Zn, Ga, Ge, As, Se, Mo)
R , R'= Various Substituents
Figure 6. Metal [5-Amino Levulinic Acid - Hydroxy Acid] Complexes

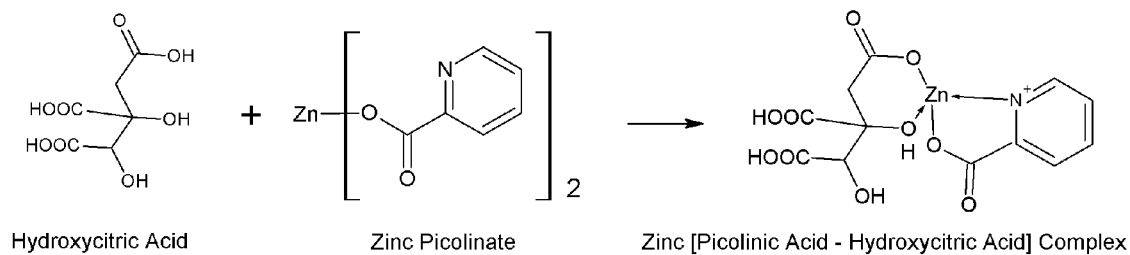
Metal [Hydroxy Acid - Picolinic Acid] Complex
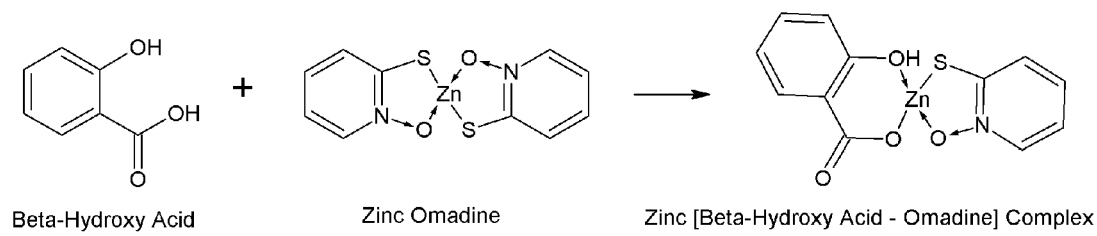
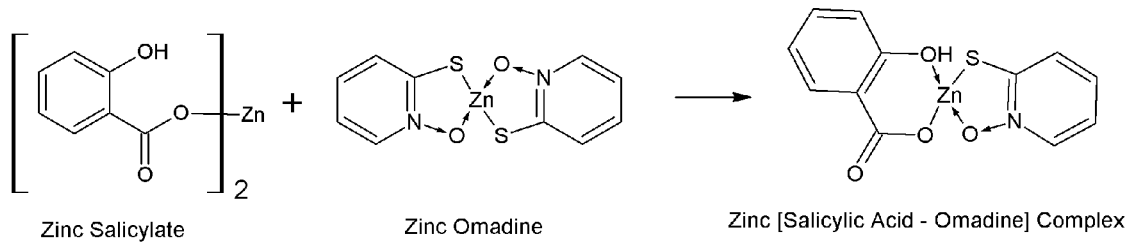
Metal [Beta-Hydroxy Acid - 2-Mercaptopyridine 1-oxide] Complex
Figure 7. Metal [Hydroxy Acid - Heterocyclic Amino Acid] Complexes

HYDROXY ACID COMPLEXES FOR ANTIAGING AND SKIN RENOVATION

This application is a continuation-in-part of U.S. patent application Ser. No. 11/307,729 filed Feb. 18, 2006. This application is also a continuation-in-part of U.S. patent application Ser. No. 10/280,519 filed Oct. 25, 2002, now abandoned. This application is also a continuation-in-part of U.S. patent application Ser. No. 10/290,933 filed Nov. 7, 2002. This application is also a continuation-in-part of U.S. patent application Ser. No. 10/394,851 filed Mar. 22, 2003, now abandoned. This application is also a continuation-in-part of U.S. patent application Ser. No. 10/439,349 filed May 15, 2003.

This invention relates to certain divalent and polyvalent d-orbital metals of first transition series of the Periodic Table of Elements, from Group IV to Group VI, and including Molybdenum; which are Ti, V, Cr, Mn, Fe, Co, Ni, Cu, Zn, Ga, Ge, As, Se, and Mo, and which are complexed concurrently with an amino acid and a hydroxy acid in a novel spirocyclic, bidentate chemical complex ("Metal Amino Acid Hydroxy Acid Complex"; FIG. 1). Upon topical application said metal complexes undergo enhanced skin penetration without causing skin irritation. The said metal complexes are useful for topical conditions that include dry skin, xerosis, ichthyosis, dandruff, brownish spots, keratoses, melasma, lentigines, age spots, dark circles around eyes, skin pigmentation, topical inflammation, liver spots, pigmented spots, wrinkles, blemishes, skin lines, oily skin, acne, warts, eczema, pruritic skin, psoriasis, inflammatory dermatoses, disturbed keratinization, dandruff, bacterial infection, fungal infection, wound healing, body odor control, and skin changes associated with aging. Also, it has been found in the present invention, surprisingly, that the divalent metals of Group IIA, for example Mg and Ca, and Group III, for example Al, do not form said spirocyclic bidentate metal complexes of FIG. 1. The chemical nomenclature of such complexes can be very difficult. For this reason, both the chemical names and their adopted or common names of some of these complexes, and their constituent moieties, are illustrated in FIG. 2.

The compositions of the present invention require the following two species, or their equivalents, in the same molecule: (i) a hydroxy acid, and (ii) a chelate or complex of an amino acid with a divalent or a polyvalent metal of the first transition series of the Periodic Table of Elements from Group IV to Group VI, and including Molybdenum; wherein metals are Ti, V, Cr, Mn, Fe, Co, Ni, Cu, Zn, Ga, Ge, As, Se, and Mo. Alternatively, as an equivalent of an amino acid, the use of a chelate of a second hydroxy acid in place of a chelate or complex of an amino acid, wherein said second hydroxy acid is not the same as the first hydroxy acid, and wherein the hydroxy group of second hydroxy acid is capable of forming a bidentate chelate structure with said metal in combination with the first hydroxy acid, leads to the formation of "metal hydroxy acid-hydroxy acid complex" of mixed hydroxy acids [FIG. 3] of unprecedented composition. The equivalent of an amino acid can also be a heterocyclic acid in which the amino group is part of the heterocyclic moiety, for example picolinic acid. Also, equivalent of an amino acid can be a heterocyclic acid in which the amino group is part of the heterocyclic moiety and the acid group is a thiol instead of a carboxylic acid, for example, omadine, or 2-Mercaptopyridine 1-oxide.

The compositions of the present invention can be made by three different processes [FIG. 3], which incorporate a novel intermolecular metal redistribution reaction. In this reaction, for example, the metal atom from an amino acid chelate or complex and in which the metal atom is bound to at least two amino acid moieties, transfers to a hydroxy acid along with one of the two amino acid moieties, and wherein the second amino acid bound to said metal atom is released as free amino acid. The free amino acid thus liberated can still remain bound to the newly formed "metal amino acid—hydroxy acid complex", depending on the electronic vacancy of the d-orbital of the metal bound to said "metal amino acid—hydroxy acid complex". In the case where a metal salt of a hydroxy acid is reacted with a metal chelate or complex of an amino acid, the metal from either amino acid moiety transfers to one of the hydroxy acid moieties bound to the metal of metal salt of hydroxy acid, or the metal atom from hydroxy acid metal salt along with one hydroxy acid moiety transfers to an amino acid moiety of the metal chelate or complex of amino acid. In this instance, one molecule of a metal salt of a hydroxy acid reacts with one molecule of the metal chelate or complex of amino acid to form two molecules of "metal amino acid-hydroxy acid complex". In the examples where a metal complex of one hydroxy acid, for example an alpha hydroxy acid, is reacted with a metal complex of a second hydroxy acid, for example a beta hydroxy acid, then the metal atom from one hydroxy acid along with one hydroxy acid moiety transfers to one of the hydroxy acid groups attached to the second metal hydroxy acid complex, or vice versa. In Process I [FIG. 3], (i) a hydroxy acid, such as an alpha hydroxy acid, is mixed with heating for a brief period with (ii) a metal amino acid chelate having said metal, in (iii) a hydroxylic solvent, such as water. In Process II [FIG. 3], alternatively, (i) a chelate or complex of an amino acid with said metal, and (ii) metal complex of a hydroxy acid, wherein said metal is the same as that in a chelate or complex of an amino acid, is mixed with heating for a brief period with a metal amino acid chelate having said metal, in (iii) a hydroxylic solvent, such as water. In Process III [FIG. 3], (i) a metal salt of a beta hydroxy acid, such as salicylic acid, is mixed with heating for a brief period with (ii) a metal complex of an alpha hydroxy acid, and wherein the said metal is same both in beta hydroxy acid and alpha hydroxy acid in (iii) a hydroxylic solvent. All of the reactions in Process I and II and III are novel in that the metal atom undergoes a rearrangement or migration from one species of component, for example an amino acid, with another species of a component, for example, hydroxy acid; or a rearrangement or migration from one species of component, for example a beta hydroxy acid, with another species of a component, for example, an alpha hydroxy acid.

[FIG. 3].

This is both surprising and unexpected since salts of hydroxy acids of certain monovalent and divalent metals of Group IA and IIA, respectively, are both well known in the prior art to penetrate skin poorly, and provide topical benefits minimally, if at all. For example, Yu et al. (U.S. patent application Ser. No. 20030017130) have clearly established problems with skin absorption of hydroxy acids and their alkali metal salts. Yu et al. disclose that there is no doubt that alpha hydroxy acids, alpha keto acids, and related compounds are therapeutically effective for topical treatment of various cosmetic conditions and dermatologic disorders including dry skin, acne, dandruff, keratoses, age spots, wrinkles, and disturbed keratinization. However, the compositions containing these acids may irritate human skin after repeated topical applications, due to the lower pH levels of the formulations. The irritation may range from a sensation of tingling, itching, and burning to clinical signs of redness and peeling. As disclosed by Yu et al., causes for such irritation may arise from the following: Upper layers of normal skin have a pH of 4.2 to 5.6, but the compositions containing most alpha hydroxy acids or alpha keto acids have pH values of less than 3.0. For example, a topical formulation containing 7.6% (1 M) glycolic acid has a pH of 1.9, as does a composition containing 9% (1 M) lactic acid. These compositions of lower pH values, on repeated topical applications, can cause a drastic pH decrease in the stratum corneum of human skin, and provoke disturbances in intercorneocyte bondings, resulting in adverse skin reactions, especially in individuals with sensitive skin. Moreover, it remains difficult to formulate a lotion, cream, or an ointment emulsion which contains a free acid form of the alpha-hydroxy acid, and which is a physically stable commercial product for cosmetic or pharmaceutical use. When a formulation containing an alpha-hydroxy acid or alpha-keto acid is reacted in equimolar or equinormal amounts with a metallic alkali, such as sodium hydroxide or potassium hydroxide, the composition becomes therapeutically ineffective. The reasons for such loss of therapeutic effects are believed to be as follows: The intact skin of humans is a very effective barrier to many natural and synthetic substances. Cosmetic and pharmaceutical agents may be pharmacologically effective by oral or other systematic administration, but many of them are much less or totally ineffective on topical application to the skin. Topical effectiveness of a pharmaceutical agent depends on two major factors: (a) bioavailability of the active ingredient in the topical preparation, and (b) percutaneous absorption, penetration, and distribution of the active ingredient to the target site in the skin. For example, a topical preparation containing 5% salicylic acid is therapeutically effective as a keratolytic, but one containing 5% sodium salicylate is not an effective product. The reason for such difference is that salicylic acid is a bioavailable form and can penetrate the stratum corneum, but sodium salicylate is not, and therefore cannot penetrate the stratum corneum of the skin. In the case of alpha-hydroxy acids, a topical preparation containing 5% glycolic acid is therapeutically effective for dry skin, but one containing 5% sodium glycolate is not effective. The same is true in case of 5% lactic acid versus 5% sodium lactate. The reason for such difference is that both glycolic acid and lactic acid are bioavailable forms and can readily penetrate the stratum corneum, but sodium glycolate and sodium lactate are not, and therefore cannot penetrate the stratum corneum of the skin.

Yu et al. additionally disclose (U.S. Pat. No. 5,702,688) that amphoteric compositions containing alpha hydroxy acids, alpha keto acids, or related compounds, and also the compositions containing dimeric or polymeric forms of hydroxy acids, overcome the aforementioned shortcomings and retain therapeutic efficacies for cosmetic conditions and dermatologic disorders. The amphoteric composition contains, in combination, an amphoteric or pseudoamphoteric compound and at least one of the alpha hydroxy acids, alpha keto acids, or related compounds. Such amphoteric system has a suitable pH, and can release the active form of an alpha hydroxy acid or alpha keto acid into the skin. The dimeric and polymeric forms of alpha, beta, or other hydroxy acids in non-aqueous compositions have a more desired pH than that of the monomeric form of the hydroxy acids. The non-aqueous compositions can be formulated and induced to release the active form of hydroxy acids after the compositions have been topically applied to the skin. The cosmetic conditions and dermatologic disorders in humans and animals, in which the amphoteric compositions containing the dimeric or polymeric forms of hydroxy acids may be useful, include dry skin, dandruff, acne, keratoses, psoriasis, eczema, pruritus, age spots, lentigines, melasmas, wrinkles, warts, blemished skin, hyperpigmented skin, hyperkeratotic skin, inflammatory dermatoses, skin changes associated with aging and as skin cleansers. Amphoteric substances by definition should behave either as an acid or a base, and can be an organic or an inorganic compound. The molecule of an organic amphoteric compound should consist of at least one basic and one acidic group. The basic groups include, for example, amino, imino, and guanido groups. The acidic groups include, for example, carboxylic, phosphoric, and sulfonic groups. Some examples of organic amphoteric compounds are amino acids, peptides, polypeptides, proteins, creatine, aminoaldonic acids, aminouronic acids, lauryl aminopropylglycine, aminoaldaric acids, neuraminic acid, desulfated heparin, deacetylated hyaluronic acid, hyalobiuronic acid, chondrosine, and deacetylated chondroitin. Inorganic amphoteric compounds are certain metallic oxides, such as aluminum oxide and zinc oxide. Although inorganic amphoteric compounds such as aluminum oxide, aluminum hydroxide, and zinc oxide may be utilized, organic amphoteric compounds have been found to be more efficient in formulating therapeutic compositions.

Yu et al. have additionally disclosed a large number of complexes of hydroxy acid with either an amphoteric metal, such as zinc oxide or aluminum oxide, or with an amphoteric organic compound, such as an amino acid (for example, Yu et al., U.S. Pat. Nos. 6,767,924; 6,384,079; 6,191,167; 6,159,485; 6,051,609; 6,046,238, 5,942,250; 5,889,054; 5,834,510; 877,212; 5,827,882; 5,807,890; 5,702,688; 5,691,378; 5,681,853; and 5,091,171). Yu et al. (U.S. Pat. Nos. 6,191,167; 6,060,512) have further disclosed that although inorganic amphoteric compounds such as aluminum oxide, aluminum hydroxide and zinc oxide may be utilized, organic amphoteric compounds have been found to be more efficient in formulating therapeutic compositions. Yu et al. have not disclosed any combinations of (i) a hydroxy acid, (ii) aluminum oxide or zinc oxide, and (iii) an amino acid in which all three species, (i), (ii), and (iii), are present.

Surprisingly, Yu et al. have also not disclosed any complexes in which both of the following two species are present: (i) a hydroxy acid, and (ii) a divalent or a polyvalent metal chelate or complex of an amino acid with the first transition series metal of the Periodic Table of Elements from Group IV to Group VI, and including Molybdenum, wherein metals are Ti, V, Cr, Mn, Fe, Co, Ni, Cu, Zn, Ga, Ge, As, Se, and Mo; and additionally, in which such complexes also retain the topical benefits without causing skin irritation or problems with formulating consumer compositions that require low pH. Yu et al. have also not disclosed any complexes in which both of the following two species are present: (i) a hydroxy acid, and (ii) a divalent or a polyvalent metal chelate or complex of another hydroxy acid, with the first transition series metal of the Periodic Table of Elements from Group IV to Group VI, and including Molybdenum, wherein metals are Ti, V, Cr, Mn, Fe, Co, Ni, Cu, Zn, Ga, Ge, As, Se, and Mo; and wherein second hydroxy acid is not the same as the first hydroxy acid, and additionally, in which such complexes also show enhanced topical benefits without causing skin irritation or problems with formulating consumer compositions that require low pH of the constituent two different hydroxy acids, when said two hydroxy acids are used in combination but not in complex form with a metal. Yu et al. have disclosed the combinations of certain salts of hydroxy acids, for example as a salt with an organic base (typically, triethanolamine) or an inorganic alkali (typically, sodium or potassium hydroxide), with amino acids (Yu et al., U.S. Pat. No. 6,384,079) or in partial salt form (Yu et al. U.S. Pat. No. 5,877,212). However, such combinations do not provide either the same composition or the superiority of any of the benefits of the present invention. A possible reason for this may be as follows. The combination of a salt of a hydroxy acid with an amino acid by Yu teachings, for example, can, at least theoretically, lead to the formation of a metal Amino acid Hydroxy Acid mixture of those two components, as shown in [FIG. 4]. Since hydroxy acid is more acidic than amino acid, the metal atom remains attached to the hydroxy acid. The amino acid, which is a weaker base than metal atom, remains unattached to the metal atom. In sharp contract, as illustrated in [FIG. 4], the process of the present invention leads to the formation of Metal Amino Acid Hydroxy Acid complex, which is not just a mixture of two components, as in Yu methodology in [FIG. 4]. This is because hydroxy acid is a stronger acid than amino acid; hydroxy acid thus replaces one of the amino acid molecules in metal chelated amino acid.

[FIG. 4].

Regardless of the accuracy of such explanation the unexpected and surprising nature of the present invention and far superiority of its skin improvement benefits over Yu teachings remain incontrovertible. Also, the "Metal Amino Acid Hydroxy Acid Complexes" of the present invention provide better bioavailability of its active agent constituents. Sodium salt of hydroxy acid, for example, upon reaching the living portion of skin cells and having reached the conditions of the pH of physiological fluid therein, which is about 7.4, can dissociate to generate hydroxy acid and sodium hydroxide [Ionization Scheme A; FIG. 5]. Since sodium hydroxide thus generated is a stronger base than the pH of physiological fluid, sodium thus tends to bind strongly with lactic acid moiety just released in the ionization process. The efficacy of lactic acid is thus reduced significantly, as it is bound with sodium atom and not available as free acid. The ionization of the "Metal Amino Acid Hydroxy Acid Complexes" of the present invention, upon such ionization under the conditions of having reached physiological pH, leads to the generation of three moieties all of which are either acidic or amphoteric in their properties and thus can exist as individual moieties uncomplexed with each other at that pH [ionization Scheme B; FIG. 5].

[FIG. 5].

This is further illustrated in the pH profile of water solutions of some of these compositions in Table 1.

TABLE 1 pH Profile of 1 M Solutions in Distilled Water

| Lactic Acid "A" | Glycine "B" | Zn Glycinate "C" | "A + B" | "A + C" |
|---|---|---|---|---|
| 1.7 | 6.3 | 6.2 | 2.9 | 4.5 |

| Salicylic Acid "D" | "D + B" | "D + C" |
|---|---|---|
| 2.4 | 3.1 | 4.3 |

The pH profile in Table 1 clearly establishes that the complexes obtained by Yu et al. by the combination of a hydroxy acid, for example lactic acid ("A"), with an amino acid, for example glycine ("B"), in equimolar ratios provides an amino acid salt, for example Glycine lactate ("A+B") in the instant case, with a skin incompatible pH of 2.9. It is additionally seen in Examples 1 to 30 of Yu et al. (U.S. patent application Ser. No. 20030017130) that the pH of a 1:1 mixture of a hydroxy acid and an amphoteric amino acid ranges from an average of 3.0 to 3.3, which is still too low for skin surface, and set forth by Yu et al., and can thus cause serious skin irritation. The complexation of lactic acid with zinc glycinate ("C") according to present invention, for example, provides the resultant "Metal Amino Acid Hydroxy Acid Complex", Zinc Glycinate Lactate ("A+C"), having a highly desirable skin compatible pH of 4.5. The complexes obtained in the present invention are thus totally different, and also superior in their skin compatibility, than those reported by Yu et al.

This invention also relates to a method of enhanced topical penetration of "Metal Amino Acid Hydroxy Acid Complex" through the upper, non-living layers of skin, and comprising; (1) said ion-pair complex is applied topically on upper, non-living layers of skin, and whereupon said complex undergoes enhanced skin penetration as said complex chemical entity without any dissociation, and (2) upon reaching lower, living layers of skin, and having reached the physiological pH of 7.4, said complex dissociates and releases its constituent active agent moieties.

This invention also relates to a method of topical treatment of skin condition by "Metal Amino Acid Hydroxy Acid Complex", which comprises; (i) the in-situ generation of said complex by mixing of (i) said Hydroxy Acid and (ii) said metal complex of an amino acid in a 1:1 molar weight percent ratio, in (iii) a solubilizing agent, and (iv) mixing temperature of from 20 degrees Celsius to 90 degrees Celsius, and (v) topical application of said composition, which contains in-situ generated "Metal Amino Acid Hydroxy Acid Complex".

There is no doubt that alpha hydroxy acids (AHA), beta hydroxy acids (BHA), poly hydroxy acids (PHA) and related compounds are therapeutically effective for topical treatment of various cosmetic conditions and dermatological disorders including dry skin, acne, dandruff, keratoses, age spots, wrinkles and disturbed keratinization. However, the compositions containing these acids may irritate human skin on repeated topical applications due to lower pH of the formulations, as discussed in detail by Santhanam et al. (US patent application Ser. No. 20020009508 and U.S. Pat. No. 6,277,881), Weinkauf et al. (U.S. Pat. No. 6,022,896) Habif et al. (U.S. Pat. No. 5,989,572), Duffy (U.S. Pat. No. 5,516,793), and Groh (U.S. Pat. No. 5,863,943). See also Kligman et al. (J. Geriatr. Dermatol. 1997; 5(3):128-131). The irritation may range from a sensation of tingling, itching and burning to clinical signs of redness and peeling. Causes for such irritation may arise, as pointed by Yu et al., from the following: Upper layers of normal skin have a pH of 4.2 to 5.6, but the compositions containing most alpha hydroxy acids have pH values of less than 3.0. These compositions of lower pH on repeated topical applications can cause a drastic pH decrease in the stratum corneum of human skin, and provoke disturbances in intercorneocyte bondings resulting in adverse skin reactions, especially to some individuals with sensitive skin. Moreover, with today's state of the art it is still very difficult to formulate a lotion, cream or ointment emulsion which contains a free acid form of the alpha hydroxy acid, and which is physically stable as a commercial product for cosmetic or pharmaceutical use. For example, Groh (U.S. Pat. No. 5,683,943) reports the use of a combination of a glycol and a quaternary ammonium surfactant to stabilize certain skin conditioner AHA compositions. The use of such surfactants may not be desirable in certain cosmetic applications, such as skin lotion, creams, paste, gel, serum, and such. Bimczok et al. (U.S. Pat. No. 5,961,999) reports the use of betaine esters in AHA compositions to provide skin compatibility. This is again very limited in application, as such betains act as surfactants and they can destabilize most skin lotion, cream, gel, and paste compositions. Yu et al. (U.S. Pat. Nos. 5,690,967 and 5,681,853) report methods for improving topical delivery of AHA by combining such acids with certain amphoteric or pseudoamphoteric ingredients, such as amino acids and peptides. However, such amphoteric ingredients usually have a free carboxyl group in their molecules, and under certain conditions of the manufacture of such compositions those carboxyl groups may get ionized and separate from their combination with AHA, thus causing product instability problems. Additionally, such amphoteric or pseudoamphoteric ingredients appear only to increase the pH of such compositions, and they do not appear to have any synergistic beneficial effect on skin. Moreover, many such amphoteric ingredients are not soluble in organic solvents commonly used in cosmetic compositions for the preparation of anhydrous systems that contain certain HA. U.S. Pat. Nos. 4,363,815; 4,380,549, and 5,091,171 (Yu et al.) claim the combination of AHA's with certain amines, such as ammonium hydroxide, organic primary, secondary or tertiary amines, such as alkyl amines, alkanolamines, diamines, dialkyl amines, dialkanolamines, dialkylalkanolamines, and alkyl dialkanolamines wherein the alkyl or alkanol substituent has from 1-to-8 carbon atoms, methylamine, ethylamine, monoethanolamine, monoisopropanol amine, ethylene-diamine, 1,2-diaminopropane, dimethylamine, diethylamine, diethanolamine, diisopropanolamine, N-methylethanolamine, N-ethylethanolamine, triethylamine, triethanolamine, N-methyidiethanolamine, and triisopropylamine. However, the use of such strongly alkaline amines, resulted in the increase of the pH of such AHA, thus resulting in their much -lowered efficacy, as proclaimed in more recent references cited above. Moreover, many of such amines have strong, objectionable odor and hence not suitable for cosmetic compositions.

A number of inventions have been reported to overcome the skin irritation problems of AHA and BHA, and still maintain their skin beneficial efficacy. Santhanam et al. (US Patent Application 20020009508) report the use of Echinacea extract as an anti-irritant to combat the skin irritation of certain HA. Habif et al. (U.S. Pat. No. 5,989,572) report the use of borage seed oil as an anti-irritant in HA compositions. Weinkauf et al. (U.S. Pat. No. 6,022,896) report the use of petroselinic acid as an anti-irritant for compositions that contain AHA. Santhanam et al. (U.S. Pat. No. 6,277,881) report the application of turmeric extract as an anti-irritant for AHA formulations. Duffy (U.S. Pat. No. 5,516,793) reports the use of ascorbic acid to reduce the irritation of AHA and BHA in topical preparations. Merianos (U.S. Pat. No. 5,728,390) reports the use of polyvinylpyrrolidone for minimizing the skin irritation effect of AHA. As is evident from the claims in the above mentioned prior art, the above methods are all very limited in their application, as they relate to the use of specific single ingredient that may not be acceptable in certain topical compositions.

The hydroxy acids are also well known for their skin beneficial properties. U.S. Pat. No. 5,861,432 (Sklar) describes the use of glycolic acid in an acne treatment formulation. Glycolic acid has been used in many cosmetic formulations for improved skin appearance. There are two main theories on how glycolic acid works. The first theory proposes that the glycolic acid produces a mild sub clinical irritation which stimulates the epidermis to produce fresh skin, while the second theory proposes that glycolic acid weakens the intercellular bonding of the corneocytes in a manner similar to both water and retinoids. Unfortunately, little objective data regarding the effectiveness of alpha-hydroxy acid (AHA), such as glycolic acid, has been published thereby leaving the industry to rely on anecdotal information, which is difficult to quantify. It is quite clear that many of the topical cosmetics incorporating glycolic acid or other alpha-hydroxy acids have insufficient concentrations to accomplish their objectives. The human skin is comprised of two principal components, the avascular epidermis and the underlying vascular dermis. The epidermis consists of four layers: the stratum corneum, stratum granulosum, stratum spinosum and stratum basale. The dermis mainly consists of collagen, elastin fibers and ground substances including glycosaminoglycan. There are two forms of skin aging: intrinsic aging, also known as chronological aging and extrinsic aging, also known as photo aging. The aging process normally involves the dermis. Bernstein et al. (U.S. patent application No. 20050084509) disclose methods for improving photoaging, acne, acne scarring and various types of sun damage by topically applying a solution containing citric acid or a low concentration of alpha-hydroxy acid.

Intrinsic aging is a degenerative process attributed to declining physiologic functions and capacities. Extrinsic aging is caused by external factors such as sunlight, radiation, and air pollution. Alpha-hydroxy acids (AHA's) have been used topically in the prior art on keratinization (epidermal layer) where the effects are clinically detectable by the formation of a new stratum corneum. AHA's also have dermal effects. Topical applications of AHA's have caused increased amounts of mucopolysaccharides and collagen and increased skin thickness without detectable inflammation. The benefits of the AHA have caused them to be incorporated into cosmetic products for purposes such as cleansing, conditioning, dry skin etc. AHA's are categorized as nontoxic and have been used as skin desquamative agents, especially in routine use for acne, wrinkles, photo aged skin and pigmented disorders. Mandelic acid, another AHA, has been claimed by Yu et al. (U.S. Pat. Nos. 5,677,339 and 5,654,336) in a topical composition for skin wrinkles reduction. Glycolic and lactic acids have been claimed in pimples and skin redness reduction compositions by Slavtcheff et al. (U.S. Pat. Nos. 5,614,201 and 5,482,710). Alliger (U.S. Pat. No. 5,516,799) describe the use of glycolic acid for treating small mouth ulcers. Shaffer et al. (U.S. Pat. No. 5,760,079) describe hydroxy acids for treating striae distensae (stretch marks). Perricone (U.S. Pat. No. 6,417,226) has claimed Hydroxytetronic acid in a skin whitening composition. Other AHA's have shown skin-whitening effects, as mentioned by Zhang et al. (US patent application Ser. No. 20020106384).

U.S. patent application Ser. No. 20050059644 (Rood et al.) discloses certain dermatological compositions that contain a combination of both a hydroxy acid and its salt. Such compositions may also contain additional agents. However, Rood et al. do not disclose any combinations of hydroxy acid with metal complex of amino acid.

U.S. Pat. No. 5,939,082 (Oblong et al.) discloses a combination of two active agents, niacinamide, an organic base, and salicylic acid, an organic acid, for example, which are useful for certain skin conditions.

Yu et al. have done extensive research in hydroxy acids topical delivery and applications area. In a most recent U.S. patent application Ser. No. 20030017130, and several prior disclosures that include a continuation of U.S. patent application Ser. No. 09/744,882, filed Feb. 1, 2001, which is in turn a continuation of U.S. patent application Ser. No. 09/510,368, filed Feb. 22, 2000, now abandoned; which in turn is a continuation of U.S. patent application Ser. No. 09/222,995, filed Dec. 30, 1998, now U.S. Pat. No. 6,051,609; which is itself in turn a continuation of U.S. patent application Ser. No. 08/926,030, filed Sep. 9, 1997, now U.S. Pat. No. 5,962,526; which is in turn a continuation of U.S. patent application Ser. No. 08/487,684, filed Jun. 7, 1995, now U.S. Pat. No. 5,691,378; which itself is a continuation of U.S. patent application Ser. No. 08/179,190, filed Jan. 10, 1994, now U.S. Pat. No. 5,470,880, which itself is a continuation of U.S. patent application Ser. No. 08/089,101, filed Jul. 12, 1993, now U.S. Pat. No.

5,389,677; which itself is a divisional of U.S. patent application Ser. No. 08/008,223, filed Jan. 22, 1993, now U.S. Pat. No. 5,665,776; which itself is a continuation of U.S. patent application Ser. No. 07/812,858, filed Dec. 23, 1991, now abandoned; which itself is a continuation of U.S. patent application Ser. No. 07/469,738, filed Jan. 1, 1990, now abandoned; which itself is a continuation of U.S. patent application Ser. No. 06/945,680, filed Dec. 23, 1986, now abandoned; these prior art methods have been disclosed, and these are quoted herein for reference only. Some of these are discussed further below to show their irrelevance to the surprising and unexpected features of the present invention.

U.S. Pat. No. 5,690,967 (Yu et al.) discloses improved topical delivery of lactic acid with certain amphoteric agents, when the pH of said composition is 4.2 or less.

U.S. Pat. No. 5,681,853 (Yu et al.) discloses improved topical delivery of hydroxy acids with certain amphoteric agents, when the pH of said composition is 4.2 or less.

U.S. Pat. No. 5,091,171 (Yu et al.) discloses improved topical delivery of hydroxy acid and polymeric hydroxy acid with certain amphoteric agents, when the pH of said composition is 4.2 or less.

Khoshdel et al. (U.S. patent application No. 20060039878) disclose certain Xanthine and alpha-hydroxy acid combinations that are particularly useful in styling hair, lengthening hair, reducing its volume and increasing the high humidity style retention. Most preferred are substituted xanthines such as caffeine, dyphylline, cafaminol theophylline, aminophylline and theobromine.

U.S. Pat. No. 5,783,601 (Tanahashi et al.) discloses certain salts of hydroxy acid with alkali metals, amines, and amphoteric agents for treating skin condition.

U.S. Pat. No. 6,677,361 (Jacobson et al.) discloses certain chemically altered forms of niacin for topical applications.

Schlegel et al. [Journal of Animal Physiology and Animal Nutrition, 90, 216 (2006)] have disclosed improved skin penetration of zinc glycinate over zinc sulfate when administered orally.

In the present invention the hydroxy acid active agent is selected from a large number of such hydroxy acids available, for example alpha hydroxy acids, beta hydroxy acids, and polyhydroxy acids, which includes Glycolic Acid, Malic Acid, Lactic Acid, Mandelic Acid, Ascorbic Acid, Phytic Acid, Salicylic Acid, Aleuritic Acid, Tartaric Acid, Citric Acid, Hydroxytetronic Acid, Glucuronic Acid, Hyaluronic Acid, Mucic Acid, Galacturonic Acid, Gluconic Acid, Saccharic Acid, Glucoheptonic Acid, alpha-Hydroxybutyric Acid, Tartronic Acid, alpha-Hydroxyisobutyric Acid, Isocitric Acid, alpha-Hydroxyisocaproic Acid, Dihydroxymaleic Acid, alpha-Hydroxyisovaleric Acid, Dihydroxytartaric Acid, beta-Hydroxybutyric Acid, Dihydroxyfumaric Acid, beta-Phenyllactic Acid, Atrolactic Acid, Galactonic Acid, Pantoic Acid, Glyceric Acid, and their derivatives, and combinations thereof.

In accordance with the present invention, the alpha hydroxy acid, the beta hydroxy acids, and the related compounds which are incorporated into complex formation with a metal complex of an amino acid for cosmetic conditions and dermatologic disorders may be classified into three groups.

The first group is organic carboxylic acids in which one hydroxyl group is attached to the alpha carbon of the acids. The generic structure of such alpha hydroxy acids may be represented as follows:

($R_a$)($R_b$)C(OH)COOH; where $R_a$ and $R_b$ are H, F, Cl, Br, alkyl, aralkyl or aryl group of saturated or unsaturated, isomeric or non-isomeric, straight or branched chain or cyclic form, having 1 to 25 carbon atoms, and in addition $R_a$ and $R_b$ may carry OH, CHO, COOH and alkoxy group having 1 to 9 carbon atoms. The alpha hydroxy acids may be present as a free acid or lactone form, or in a salt form with an organic base or an inorganic alkali. The alpha hydroxy acids may exist as stereoisomers as D, L, and DL forms when $R_a$ and $R_b$ are not identical. Typical alkyl, aralkyl and aryl groups for Ra and Rb include methyl, ethyl, propyl, isopropyl, butyl, pentyl, octyl, lauryl, stearyl, benzyl, phenyl, etc. The alpha hydroxy acids of the first group may be divided into (1) alkyl alpha hydroxy acids, (2) aralkyl and aryl alpha hydroxy acids, (3) polyhydroxy alpha hydroxy acids, and (4) polycarboxylic alpha hydroxy acids. The following are representative alpha hydroxy acids in each subgroup.

(1) Alkyl Alpha Hydroxy acids. 2-Hydroxyethanoic acid (Glycolic acid, hydroxyacetic acid); 2-Hydroxypropanoic acid (Lactic acid); 2-Methyl 2-hydroxypropanoic acid (Methyllactic acid); 2-Hydroxybutanoic acid; 2-Hydroxypentanoic acid; 2-Hydroxyhexanoicacid; 2-Hydroxyheptanoic acid; 2-Hydroxyoctanoic acid; 2-Hydroxynonanoic acid; 2-Hydroxydecanoic acid; 2-Hydroxyundecanoic acid; 2-Hydroxydodecanoic acid (Alpha hydroxylauric acid); 2-Hydroxytetradecanoic acid (Alpha hydroxymyristic acid); 2-Hydroxyhexadecanoic acid (Alpha hydroxypalmitic acid); 2-Hydroxyoctadecanoic acid (Alpha hydroxystearic acid); and 2-Hydroxyeicosanoic acid (Alpha hydroxyarachidonic acid).

(2) Aralkyl and Aryl Alpha Hydroxy acids. 2-Phenyl 2-hydroxyethanoic acid (Mandelic acid); 2,2-Diphenyl 2-hydroxyethanoic acid (Benzilic acid); 3-Phenyl 2-hydroxypropanoic acid (Phenyllactic acid); 2-Phenyl 2-methyl 2-hydroxyethanoic acid (Atrolactic acid); 2-(4'-Hydroxyphenyl) 2-hydroxyethanoic acid (4-Hydroxymandelic acid); 2-(4'-Chiorophenyl) 2-hydroxyethanoic acid (4-Chloromandelic acid); 2-(3'-Hydroxy-4'-methoxyphenyl) 2-hydroxyethanoic acid (3-Hydroxy-4-methoxymandelic acid); 2-(4'-Hydroxy-3'-methoxyphenyl) 2-hydroxyethanoic acid (4-Hydroxy-3-methoxymandelic acid); 3-(2'-Hydroxyphenyl) 2-hydroxypropanoic acid [3(2'-Hydroxyphenyl) lactic acid]; 3-(4'-Hydroxyphenyl) 2-hydroxypropanoic acid [3-(4'-Hydroxyphenyl) lactic acid]; and 2-(3', 4'-Dihydroxyphenyl) 2-hydroxyethanoic acid (3,4-Dihydroxymandelic acid).

(3) Polyhydroxy Alpha Hydroxy acids. 2,3-Dihydroxypropanoic acid (Glyceric acid); 2,3,4-Trihydroxybutanoic acid (Isomers; erythronic acid, threonic acid); 2,3,4,5-Tetrahydroxypentanoic acid (Isomers: ribonic acid, arabinoic acid, xylonic acid, lyxonic acid); [2,3,4,5,6-Pentahydroxyhexanoic acid (Isomers: allonic acid, altronic acid, gluconic acid, manrioic acid, gulonic acid, idonic acid, galactonic acid, talonic acid); and 2,3,4,5,6,7-Hexahydroxyheptanoic acid (Isomers: glucoheptonic acid, galactoheptonic acid etc.).

(4) Polycarboxylic Alpha Hydroxy acids. 2-Hydroxypropane-1,3-dioic acid (Tartronic acid); 2-Hydroxybutane-1,4-dioic acid (Malic acid); 2,3-Dihydroxybutane-1,4-dioc acid (Tartaric acid); 2-Hydroxy-2-carboxypentane-1,5-dioic acid (Citric acid); and [2,3,4,5-Tetrahydroxyhexane-1,6-dioic acid (Isomers; saccharic acid, mucic acid etc.); hydroxycitric acid, Garcinia acid, and Garcinol.

(5) Lactone Forms. The typical lactone forms are gluconolactone, galactonolactone, glucuronolactone, galacturonolactone, gulonolactone, ribonolactone, saccharic acid lactone, pantoyllactone, glucoheptonolactone, mannonolactone, Garcinia Lactone, and galactoheptonolactone.

Zinc salts of certain polyhydroxy acids are well known for their anti-acne benefits. For example, Dreno et al. [Eur. J. Dermatol. 15, 152 (2005)] report zinc gluconate in controlling resistant variety of Propionibacteriaum acnes (acne bacteria). Maynerdier [Eur. J. Dermatol., 10, 269 (2000)] reports efficacy of zinc gluconate in the treatment of inflammatory acne. Stephan et al. [Ann. Dermatol. Verereol., 131, 455 (2004)] report zinc salts in dermatology. Dutiel et al. [Ann. Dermatol. Venereol., 132, 219 (2005)] report photosensitization potential of zinc gluconate for acne treatment. In a surprising and unexpected discovery, the trace metal complexes of amino acid-gluconic acid have superior anti-acne benefits that zinc gluconate.

The metal derivative of an amino acid is selected from iron, or copper, or zinc, or manganese, or chromium, or cobalt, or selenium, or vanadium, or molybdenum complexed with glycine, or alanine, or beta-alanine, or valine, or leucine, or isoleucine, or phenylalanine, or alpha-amino butyric acid, or C-phenylglycine, or C-hydroxyphenylglycine, or proline, or tryptophane, or lysine, or ornithine, or arginine, or histidine, or citrulline, or glutamic acid, or aspartic acid, or serine, or threonine, or hydroxyproline, or tyrosine, or dihydroxytyrosine, or cysteine, or cystine, or methionine, or homocysteine, or lanthionine, or amino levulinic acid. Amino acid can also be a heterocyclic amino acid, such as picolinic acid (2-Pyridinecarboxylic acid).

Amino Levulinic Acid, also known as 5-amino levulinic acid, or delta-amino levulinic acid, is well known for its anti-acne activity in combination with photodynamic therapy [Gold et al., Dermatol. Surg., 8, 1077 (2004); Pollock et al., Br. J. Dermat., 151, 616 (2004); Taub, J. Drugs Dermatol., 3, S15 (2004); Wiegell et al., J. Am. Acd. Dermatol., 54, 647 (2006)]. In a surprising discovery of the present invention, the zinc complexes of amino levulinic acid and an alpha hydroxy acid or a beta hydroxy acid [FIG. 6] provide topical acne benefits without any combinatorial photodynamic laser therapy.

[FIG. 6].

The amino acid can also be a heterocyclic amino acid, such as picolinic acid (2-pyridinecarboxylic acid). For example, the combination of zinc picolinate and hydroxycitric acid, or an alkali or alkaline earth salt of hydroxycitric acid, provides the Zinc picolinate hydroxycitrate complex [FIG. 7]. Hydroxycitric acid, or its salt, in this example, can also be in a botanical extract form, for example, an extract of Garcinia Cambogia plant. The amino acid can be an amino acid equivalent, such as omadine (2-mercaptopyridine 1-oxide). The combination of zinc omadine and a beta-hydroxy acid, for example, results in the formation of zinc [Beta-Hydroxy Acid-2-Mercaptopyridine 1-oxide]Complex. The reaction of zinc salicylate, a beta-hydroxy acid salt, with zinc omadine, similarly, results in the formation of two molecules of zinc [Salicylic Acid-Omadine] Complex [FIG. 7].

[FIG. 7].

The preferred pH of the "Metal Amino Acid Hydroxy Acid Complex" of the present invention is from about 4.0 to about 7.5, preferably from about 4.5 to about 6.5. The preferable pH is determined by the optimum stability of said complex. For example, Table 2 summarizes the pH profile of individual active agents and their said complexes derived from said active agents. The preparation of "Metal Amino Acid Hydroxy Acid Complex" was done in-situ in a deionized water solution by mixing 0.01 mole of hydroxy acid in 50 grams of deionized water and then determining the pH of the resulting solution, then preparing a solution of 0.01 mole of a metal complex of an amino acid in 50 grams of deionized water and determining its pH. The solution of hydroxy acid in water thus obtained is then combined with the solution of metal complex of amino acid in water as obtained above, which provides a solution of "Metal Amino Acid Hydroxy Acid Complex" in deionized water, the pH of which is determined.

TABLE 2 pH Profile of "Metal Amino Acid Hydroxy Acid Complex".

| Hydroxy Acid "A" (pH) | Metal Amino Acid "B" (pH) | "A + B Complex" (pH) |
|---|---|---|
| Lactic Acid (1.6) | Zn Glycinate•H2O (6.3) | "Zn Glycinate Lactate" (4.6) |
| Lactic Acid (1.6) | Cu Glycinate (8.9) | "Cu Glycinate Lactate" (4.3) |
| Lactic Acid (1.6) | Mn Glycinate (8.0) | "Mn Glycinate Lactate" (4.3) |
| Salicylic Acid (2.4) | Zn Glycinate (6.3) | "Zn Glycinate Salicylate" (4.3) |
| Salicylic Acid (2.4) | Zn Bis-Arginate•HCl | "Zn Arginate Salicylate" (4.7) |
| Ascorbic Acid (2.0) | Zn Glycinate•H2O (6.3) | "Zn Glycinate Ascorbate" (4.7) |

The solubility properties of "Metal Amino acid Hydroxy acid" complexes of the present invention are, surprisingly, much greater than hydroxy acids of low solubility. For example, salicylic acid has a solubility of only 0.2% at 20 C in water. The solubility is only 2.0% at 80 C in water. However, the solubility of Zinc Glycinate Salicylate is over 20.0% even at 35 C. Zinc Arginate Salicylate has a solubility of over 20.0% at 35 C. This improvement in solubility is beneficial both for the increased bioavailability, as noteworthy in Example 8 and Example 10, and ease of formulation (several Examples) and stability (Example 11) of these complexes.

In the compositions of the present invention, additional skin, hair, and body beneficial ingredients, such as other anti-aging ingredients, vitamins, hormones, analgesics, anesthetics, sun screens, skin whiteners, anti-acne agents, anti-bacterial agents, anti-fungal agents, botanical extracts, pharmaceuticals, processing-aids, minerals, plant extracts, concentrates of plant extracts, emollients, moisturizers, skin protectants, humectants, silicones, skin soothing ingredients, colorants, perfumes, and like.

The compositions of the present invention can be formulated in various cosmetic and pharmaceutical consumer products utilizing a variety of delivery systems and carrier bases. Such consumer product forms include the group consisting of shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, band-aids, and balms.

In another preferred aspect, the delivery system or a carrier base are selected in the form of a lotion, cream, gel, spray, thin liquid, body splash, powder, compressed powder, tooth paste, tooth powder, mouth spray, paste dentifrice, clear gel dentifrice, mask, serum, solid cosmetic stick, lip balm, shampoo, liquid soap, bar soap, bath oil, paste, salve, collodion, impregnated patch, impregnated strip, skin surface implant, impregnated or coated diaper, and similar delivery or packaging form.

In another preferred aspect, the delivery system can be human body or hair deodorizing solution, deodorizing powder, deodorizing gel, deodorizing spray, deodorizing stick, deodorizing roll-on, deodorizing paste, deodorizing cream, deodorizing lotion, deodorizing aerosol, and other commonly marketed human body and hair deodorizing compositions, household deodorizing solution, deodorizing powder, deodorizing gel, deodorizing spray, carpet deodorizer, room deodorizer, and other commonly marketed household deodorizing compositions, animals and pets deodorizing solution, deodorizing powder, deodorizing gel, deodorizing spray, animals and pets carpet deodorizer, animals and pets room deodorizer, and other commonly marketed animal and pet deodorizing compositions.

In another preferred aspect, the delivery system can be traditional water and oil emulsions, suspensions, colloids, micro-emulsions, clear solutions, suspensions of nanoparticles, emulsions of nanoparticles, or anhydrous compositions.

Additional cosmetically or pharmaceutically beneficial ingredients can also be included in the formulated compositions of the present invention, which can be selected from, but not limited to skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In another preferred aspect, the cosmetically acceptable composition further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylans, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitin, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, crosslinked dextrans, dextrin, emulsan, ethyl hydroxyethyl cellulose, flaxseed saccharide (acidic), galactoglucomannans, galactomainans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994), which is incorporated entirely by reference. Complex carbohydrates found in Kirk-Othmer Encyclopedia of Chemical Technology, Fourth Edition, Vol. 4, John Wiley and Sons, NY pp. 930-948, 1995 which is herein incorporated by reference.

The cosmetically acceptable composition of this invention may include surface-active agents. Surface-active agents include surfactants, which typically provide detersive functionality to a formulation or act simply as wetting agents. Surface-active agents can generally be categorized as anionic surface-active agents, cationic surface-active agents, non-ionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, for example, sulfur trioxide or oleum, obtained according to known sulfonation methods, including bleaching and hydrolysis. Preferred are alkali metals and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecylbenzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL. as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, Cocotrimonium chloride, Cethethyidimonium bromide, Dibehenyidimonium chloride, Dihydrogenated tallow benzylmonium chloride, disoyadimonium chloride, Ditallowdimonium chloride, Hydroxycetyl hydroxyethyl dimonium chloride, Hydroxyethyl Behenamidopropyl dimonium chloride, Hydroxyethyl Cetyidimonium chloride, Hydroxyethyl tallowdimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryidimonium chloride, cetalkonium chloride, dicetyidimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions may include long chain fatty amines from about $C_{10}$ to $C_{22}$ and their derivatives. Specific examples include dipalmitylamine, lauramidopropyidimethylamine, and stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of the present invention, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH $(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning, Midland, Mich., USA. Additional alkyl and phenyl silicones may be employed to enhance moisturizing properties. Resins such as dimethicone (and) trimethylsiloxysilicate or Cyclomethicone (and) Trimethylsiloxysilicate fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, C.sub.12 to C.sub.16 fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane end blocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane-200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., and from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol. 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, Germany. When used, the silicone surfactants are preferably included in the formulations of this invention at a concentration of 0.1 to 30 weight percent, more preferably 1 to 15 weight percent. Amine functional silicones and emulsions may be utilized in the present invention. Preferred examples include Dow Corning 8220, Dow Corning 939, Dow Corning 949, Dow Corning 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about C.sub.6 to C.sub.22 atoms. A preferred volatile hydrocarbon is an aliphatic hydrocarbon having a chain length from about C.sub.6 to C.sub.16 carbon atoms. An example of such compound includes isohexadecane, under the trade name Permethyl 101A, available from Presperse, South Plainfield, N.J., USA. Another example of a preferred volatile hydrocarbon is C.sub.12 to C.sub.14 isoparaffin, under the trade name Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17 Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers that can be used in this invention include high molecular weight crosslinked homopolymers of acrylic acid, and Acrylates/C10-30 Alkyl Acrylate Crosspolymer, such as the Carbopol and Pemulen series, both available from B. F. Goodrich, Akron, Ohio, USA; anionic acrylate polymers such as Salcare and cationic acrylate polymers such as Salcare SC96, available from Ciba Specialties, High Point, N.C., USA; Acrylamidopropyltrimonium chloride/acrylamide; Hydroxyethyl methacrylates polymers, Steareth-10 Allyl Ether/Acrylate Copolymer; Acrylates/Beheneth-25 Metacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The antioxidants will be present at from 0.01 to 20 weight percent, preferably 0.5 to 10 weight percent and most preferably from 1.0 to 5.0 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexy 1-2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Example of preservatives, which may be used include, but are not limited to 1,2-dibromo-2,4-dicyano butane (Methyidibromo Glutaronitrile, known as MERGUARD. Nalco Chemical Company, Naperville, Ill., USA), benzyl alcohol, imidazolidinyl urea, 1,3-bis (hydroxymethyl)-5,5-dimethyl-2,3-imidazolidinedione (e.g., DMDM Hydantoin, known as GLYDANT, Lonza, Fairlawn, N.J., USA.), methylchloroisothiazolinone and methylisothiazolinone (e.g., Kathon, Rohm & Haas Co., Philadelphia, Pa., USA), methyl paraben, propyl paraben, phenoxyethanol, sodium benzoate, Ethylhexylglycerin, Natamycin, Nicin, Hexamidine Diisethionate, Triclocarban, Triclosan, zinc omadine, Benzalkonium chloride, Zinc glycine salicylate, Azelaic acid, Zinc Azelate, and Zinc salicylate, and mixtures thereof.

The cosmetically acceptable composition of this invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerin, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. from 0.1 to 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, humectants, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the dispersion polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, Carbopol-type acrylic acid thickeners available from B.F. Goodrich; xanthan gums; sodium alginates; gum arabic; cellulose derivatives and poly-(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acryinitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

The cosmetic compositions of this invention may be formulated in a wide variety of form, for non-limited example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. In detail, the cosmetic composition of the present invention can be provided in a form of skin softener (skin lotion), astringent lotion, nutrient emulsion (milk lotion), nutrient cream, message cream, essence, eye cream, cleansing cream, cleansing foam, cleansing water, facial pack, spray or powder.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonite, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane, butane, diethyl ether, or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension may comprise liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminum metahydroxide, bentonite, agar and tragacanth or mixtures of these ingredients.

The formulation of cleansing compositions with surfactant may comprise aliphatic alcohol sulfate, aliphatic alcohol ether sulfate, sulfosucinnate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester or mixtures of these ingredients.

Additional antioxidant ingredients and compositions can be selected from, but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), α-Lipoic acid, Niacinamide lipoate, Glutathione, Andrographolide (*Andrographis paniculata*), Carnosine, Niacinamide, *Potentilla erecta* extract, Polyphenols, Grapeseed extract, Pycnogenol (Pine Bark extract), Pyridoxine, Magnolol, Honokiol, Paeonol, Resacetophenone, Quinacetophenone, arbutin, kojic acid, and combinations thereof.

The blood micro-circulation improvement ingredients and compositions can be selected from, but not limited to, Horse Chestnut Extract (*Aesculus hippocastanum* extract), Esculin, Escin, Yohimbine, Capsicum Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), Boswellia Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (*Vitis Vinifera*) leaves, apigenin, phytosan, luteolin, and combinations thereof.

The anti-inflammatory ingredients or compositions can be selected from, but not limited to, at least one antioxidant class of Cyclo-oxygenase (for example, COX-1 or COX-2) or Lipoxygenase (for example, LOX-5) enzyme inhibitors such as Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, and Emblica extract. Anti-inflammatory composition can additionally be selected from, but not limited to, Horse Chestnut Extract (*Aesculus hippocastanum* extract)), Esculin, Escin, Yohimbine, Capsicum Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), *Emblica* extract (*Phyllanthus emblica* extract), Asiaticoside (*Centella asiatica* extract), Boswellia Extract (*Boswellia serrata*), Sericoside, Visnadine, Thiocolchicoside, Grapeseed Extract, Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (*Vitis Vinifera*) leaves, apigenin, phytosan, luteolin, and combinations thereof.

EXAMPLES

The following examples are presented to illustrate presently preferred practice thereof. As illustrations they are not intended to limit the scope of the invention. All amounts are in weight percent.

Example 1

Preparation of Zinc Glycinate Lactate Complex

| 1 | Zinc Glycinate•H2O | 23.1 |
|---|---|---|
| 2 | Lactic Acid, 85% | 10.0 |
| 3 | Water | 66.9 |

Procedure: Mix all ingredients and heat at 80 to 90 C for 2 hours. A clear solution is obtained. Evaporate to ⅓ of volume and cool. Add 50.0 mL of ethanol with mixing. Filter and wash with ethanol. A white, hygroscopic solid is obtained. It is dried in a desiccator. It does not have any smell of lactic acid. Ir spectrum shows strong peaks at 1584, 1412, 1319, 1122, 1046 cm−1. Zinc glycinate, for comparison, has strong ir peaks at 290, 1573, 1399, 1317, 1046, 903 cm−1.

Example 2

Alternate Preparation of Zinc Glycinate Lactate Complex via Zinc Lactate

| 1 | Zinc Glycinate•H2O | 6.0 |
|---|---|---|
| 2 | Zinc Lactate•2H2O | 7.0 |
| 3 | Water | 87.0 |

Procedure: Mix all ingredients and heat at 80 to 90 C for 2 hours. A clear solution is obtained. Evaporate to ⅓ of volume and cool. Add 50.0 mL of ethanol with mixing. Filter and wash with ethanol. A white, hygroscopic solid is obtained. It is dried in a desiccator. It does not have any smell of lactic acid. Ir (ethanol cast film) 1577, 1407, 1320, 1120, 1046 cm−1. In comparison, Zinc Lactate Ir (ethanol cast film) 1550, 1520, 1317, 1266, 1120, 1042 cm−1.

Example 3

Preparation of Zinc Glycinate Salicylate Complex

| 1 | Zinc Glycinate•H2O | 12.0 |
|---|---|---|
| 2 | Salicylic Acid | 7.0 |
| 3 | Water | 81.0 |

Procedure: Mix all ingredients and heat at 80 to 90 C for 1 hour. A clear solution is obtained. Evaporate to ⅓ of volume and cool. Add 50.0 mL of ethanol with mixing. Filter and wash with ethanol. A white solid is obtained. It is dried in a desiccator. Ir spectrum shows strong peaks at 1574, 1504, 1498, 1394, 1319, 1118, 1042, 900, 701 cm−1.

Example 4

Alternate Preparation of Zinc Glycinate Salicylate Complex

| 1 | Zinc Salicylate | 17.0 |
|---|---|---|
| 2 | Glycine | 8.0 |
| 3 | Water | 75.0 |

Procedure: Mix all ingredients and heat at 80 to 90 C for 1 hour. A clear solution is obtained. Evaporate to ⅓ of volume and cool. Add 50.0 mL of ethanol with mixing. Filter and wash with ethanol. A white solid is obtained. It is dried in a desiccator. Ir (Ethanol cast film) 1588, 1459, 1386, 1339, 1240, 1152, 1034, 752 cm−1. In comparison, Zinc Salicylate Ir (ethanol cast film) 1590, 1567, 1463, 1382, 1337, 1232, 875, 815, 753, 676 cm−1.

Example 5

Alternate Preparation of Zinc Glycinate Salicylate Complex via Zinc Glycinate

| | | |
|---|---|---|
| 1 | Zinc Glycinate•H2O | 12.0 |
| 2 | Zinc Salicylate | 17.0 |
| 3 | Water | 71.0 |

Procedure: Mix all ingredients and heat at 80 to 90 C for 1 hour. A clear solution is obtained. Evaporate to ⅓ of volume and cool. Add 50.0 mL of ethanol with mixing. Filter and wash with ethanol. A white solid is obtained. Ir (Ethanol cast film) 1591, 1481, 1460, 1393, 1338, 1248, 1152, 759 cm−1.

Example 6

Preparation of Zinc Arginate Salicylate Complex

| | | |
|---|---|---|
| 1 | Zinc Bis-Arginate•HCl | 22.4 |
| 2 | Salicylic Acid | 7.0 |
| 3 | Water | 70.6 |

Procedure: Mix all ingredients and heat at 80 to 90 C for 1 hour. A clear solution is obtained. Evaporate to ⅓ of volume and cool. Add 50.0 mL of ethanol with mixing. Filter and wash with ethanol. A hygroscopic solid is obtained. It is dried in a desiccator. Ir spectrum shows strong peaks at 1622, 1575, 1392, 1086, 1043 cm−1.

Example 7

Preparation of Zinc Glycinate Ascorbate Complex

| | | |
|---|---|---|
| 1 | Zinc Glycinate•H2O | 11.5 |
| 2 | Ascorbic Acid | 9.0 |
| 3 | Water | 79.5 |

Procedure: Mix all ingredients and heat at 40 to 50 C for 1 hour. A clear solution is obtained. Evaporate to ⅓ of volume and cool. Add 50.0 mL of ethanol with mixing. Filter and wash with ethanol. A white solid is obtained. It is dried in a desiccator. Ir spectrum shows strong peaks at cm−1.

Example 8

Skin Penetration of Zinc Glycinate Lactate (from Example 1)

Procedure. A 0.1 molar solution of ingredients in a mixture of glycerin and water was applied on a synthetic membrane, which was placed over a Franz Diffusion Cell. The ingredients migrating to the phosphate buffer part of diffusion cell were quantified. % Penetration is based on the amount of ingredient applied to synthetic membrane. The results are tabulated below.

| | | |
|---|---|---|
| 1 | Zinc Glycinate Lactate | 75% |
| 2 | Glycine + Lactate Acid | 40% |
| 3 | Lactic Acid | 25% |
| 4 | Sodium Lactate | 20% |
| 5 | Zinc Lactate | 50% |

Example 9

Preparation of Zinc Glycinate Lactate Cosmetic Serum

| | | |
|---|---|---|
| 1 | Zinc Glycinate•H2O | 23.1 |
| 2 | Lactic Acid, 85% | 10.0 |
| 3 | Water | 50.9 |
| 4 | Glycerin | 10.0 |
| 5 | Silicone Wax Emulsion | 5.0 |
| 6 | Preservative | 1.0 |

Procedure: Mix 1 to 5 at 60 to 70 C for one hour. Cool to room temperature. Add 6 and mix. A syrupy product is obtained.

Example 10

Skin Penetration of Zinc Glycinate Salicylate (from Example 2)

Procedure. A 0.1 molar solution of ingredients in a mixture of ethanol and water was applied on a synthetic membrane, which was placed over a Franz Diffusion Cell. The ingredients migrating to the phosphate buffer part of diffusion cell were quantified. % Penetration is based on the amount of ingredient applied to synthetic membrane. The results are tabulated below.

| | | |
|---|---|---|
| 1 | Zinc Glycinate Salicylate | 65% |
| 2 | Glycine + Salicylic Acid | 35% |
| 3 | Salicylic Acid | 15% |
| 4 | Sodium Salicylate | 10% |
| 5 | Zinc Salicylate | 25% |

Example 11

Stability Testing of Zinc Glycinate Lactate Complex of Example 1

Method: The material of Example 1 was stored at 50 C oven in a sealed glass container. After two months the material was off-white. A calorimetric reading with a color meter, such as Hunter Color Meter, shows that the color reading has changed by only 5%, and the product is still stable, and has not separated into solid and liquid phases. The color meter readings were L 96.43, a −1.03, b 0.46.

Example 12

Zinc Glycinate Lactate Complex in a Facial Gel Base

| | | |
|---|---|---|
| 1 | Zinc Glycinate Lactate | 5.0 |
| 2 | PEG-6 | 46.5 |
| 3 | NH4 Acryloylmethyltaurate | 1.0 |
| 4 | Diglycerol | 4.0 |
| 5 | Silicone Wax | 6.0 |
| 6 | Deionized Water | 20.0 |
| 7 | Glycerin | 5.0 |
| 8 | Preservative | 0.5 |
| 9 | Vitamin E | 2.0 |
| 10 | Dimethicone | 4.0 |
| 11 | Dimethiconol | 4.0 |
| 12 | Cetyl Dimethiconol | 2.0 |

Procedure: The ingredients 3 and 6 were mixed and heated at 40 to 50 C for 30 minutes. All other ingredients were then added to it with mixing. The composition was cooled to room temperature. A translucent gel was obtained.

Example 13

The In-Situ Preparation of 55% High Potency Zinc Gluconate Glycinate Complex via an Alternate Method in a Cosmetic Serum Base

| | | |
|---|---|---|
| 1 | Zn Gluconate | 45.6 |
| 2 | Na Glycinate•H2O | 9.7 |
| 3 | Sorbitol | 10.0 |
| 4 | Water | 33.7 |
| 5 | Preservative | 1.0 |

Procedure: All ingredients were mixed and heated at 40 to 50 C for 30 minutes. The product was cooled. A serum-like composition was obtained.

Example 14

The In-Situ Process of a 34.0% High Potency Anti-aging and Skin Whitening Zinc Lactate Glycinate Composition via Alternate Method

| | | |
|---|---|---|
| 1 | Zinc Lactate | 24.3 |
| 2 | Na Glycinate•H2O | 9.7 |
| 3 | Diglycerol | 10.0 |
| 4 | Deionized Water | 50.0 |
| 5 | Silicone Emulsion | 5.0 |
| 6 | Preservative | 1.0 |

Procedure: All ingredients were mixed at 50 to 60 C. A composition containing in-situ formed Zinc Glycinate Lactate Complex was obtained.

Example 15

In-Situ Generated Zinc Glycinate Salicylate Complex in a Cosmetic Gel Base

| Ingredient | % |
|---|---|
| 1. PEG-6 | 57.92 |
| 2. Aristoflex AVC | 1.0 |
| 3. Glycerin | 5.0 |
| 4. Water | 20.0 |
| 5. Preservative | 0.5 |
| 6. Vitamin E | 0.5 |
| 7. Zn Glycinate•H2O | 2.3 |
| 8. Salicylic Acid | 1.38 |
| 9. Dimethicone | 4.0 |
| 10. Dimethiconol | 4.0 |
| 11. Cetyl Dimethiconol | 2.0 |
| 12. *Galanga* Ext. | 0.2 |
| E13. Esculin | 0.5 |
| 14. *Boswellia Serrata* Ext. | 0.2 |
| 15. Methylsulfonylmethane | 0.5 |

Procedure: Mix all ingredients in Column 1 and heat at 60 to 70 C for 30 minutes. Cool to room temperature. A clear pale yellow gel of composition was obtained.

Example 16

In-Situ Process of a Mixture of Zinc Glycinate Lactate, Zinc Glycinate Ascorbate, and Zinc Glycinate Salicylate in a Cosmetic Gel Base

| Ingredient | Column 1 |
|---|---|
| 1. Glycerin | 54.26 |
| 2. Zn Glycinate•H2O | 6.9 |
| 3. Water | 20.0 |
| 4. Preservative | 0.5 |
| 5. Dow Corning 2501 | 10.0 |
| 6. Structure Plus | 4.0 |
| 7. Eyebright Ext. | 0.1 |
| 8. Botanical Ext. | 0.1 |
| 9. Vitamin E | 0.1 |
| 10. Lactic Acid | 0.9 |
| 11. Ascorbic Acid | 1.76 |
| 12. Salicylic Acid | 1.38 |

Procedure: All the ingredients in column 1 were mixed and heated at 60 to 70 C for 30 minutes. The product is obtained as a light yellow gel, useful for face and neck zone anti-acne, anti-age and anti-wrinkle applications. The product has the pH of 4.5.

BRIEF DESCRIPTION OF THE DRAWINGS

[FIG. 1]. Metal Hydroxy Acid Complexes.
[FIG. 2]. Nomenclature of Chemical Structures.
[FIG. 3]. Processes for Metal [Amino Acid-Hydroxy Acid] Complex and Metal [Hydroxy Acid-Hydroxy Acid] Complex.
[FIG. 4]. Yu Composition for Hydroxy Acid Salt and Amino Acid Combination.

[FIG. 5]. Ionization of Hydroxy Acid Sodium Salt and Zinc [Amino Acid-Hydroxy Acid] Complex.

[FIG. 6]. Metal [5-Amino Levulinic Acid-Hydroxy Acid] Complexes.

[FIG. 7]. Metal [Hydroxy Acid-Heterocyclic Amino Acid] Complexes.

What is claimed is:

1. The metal amino acid hydroxy acid complex zinc glycinate glycolate.

2. A composition for the treatment of dermatological disorders comprising the compound of claim 1.

3. A composition according to claim 2, wherein said dermatological disorder is selected from the group consisting of dry skin, xerosis, ichthyosis, dandruff, brownish spots, keratoses, melasma, lentigines, age spots, liver spots, pigmented spots, dark circles under the eyes, skin pigmentation, dark skin, skin wrinkles, blemishes, skin lines, oily skin, acne, warts, eczema, pruritic skin, psoriasis, inflammatory dermatoses, topical inflammation, disturbed keratinization, skin changes associated with aging, nail or skin requiring cleansers, conditioning or treatment, and hair or scalp requiring shampooing or conditioning, and combinations thereof.

4. A composition according to claim 2, further comprising carrier or base.

5. A composition according to claim 2, wherein the composition has a pH greater than or equal to 3.5 but less than or equal to 7.5.

6. A composition according to claim 3, wherein said dermatological disorder is dandruff.

7. A composition according to claim 3, wherein said dermatological disorder is skin changes associated with aging, or wrinkles.

8. A composition according to claim 3, wherein said dermatological disorder is dark circles around eyes.

9. A composition according to claim 3, wherein said dermatological disorder is skin lines.

10. A composition according to claim 3, wherein said dermatological disorder is acne.

11. A process for preparing zinc glycinate glycolate comprising: mixing (1) glycolic acid, and (2) a complex of zinc with glycine, and (3) a solubilizer, wherein the glycolic acid and the complex of zinc with glycine are present in about equimolar amounts, and wherein the glycolic acid and complex of zinc with glycine undergo a reaction to form zinc glycinate glycolate.

12. A method of treating aging related skin conditions comprising topically applying to the skin, for a period of time and in an amount sufficient to effect changes in the dermis, of a composition comprising zinc glycinate glycolate of claim 1.

13. A method according to claim 12, wherein said composition comprising zinc glycine glyconate a pH more than or equal to 3.5 but less than or equal to 7.5.

14. A method according to claim 12, wherein said method causes the reduction of pigmented and non-pigmented age spots.

15. A method according to claim 12, wherein said method causes an increase in skin thickness.

16. A method according to claim 12, wherein said method stimulates synthesis of a dermal component selected from the group consisting of glycosaminoglycans, proteoglycans, collagen and elastic fibers.

17. A method according to claim 12, wherein said method reduces dandruff.

18. A method according to claim 12, wherein said method treats bacterial infection.

19. A method according to claim 12, wherein said method treats fungal infection.

20. A method according to claim 12, wherein said method accelerates wound healing.

21. A method according to claim 12, wherein said method reduces body odor.

* * * * *